(12) United States Patent
Hartl et al.

(10) Patent No.: US 11,883,507 B2
(45) Date of Patent: *Jan. 30, 2024

(54) EXPRESSION CASSETTE WITH A SYNP160 PROMOTER

(71) Applicant: Friedrich Miescher Institute for Biomedical Research, Basel (CH)

(72) Inventors: Dominik Hartl, Birsfelden (CH); Josephine Juettner, Basel (CH); Arnaud Krebs, Habsheim (FR); Botond Roska, Oberwil (CH); Dirk Schuebeler, Basel (CH)

(73) Assignee: Friedrich Miescher Institute for Biomedical Research, Basel (CH)

( * ) Notice: Subject to any disclaimer, the term of this patent is extended or adjusted under 35 U.S.C. 154(b) by 249 days.

This patent is subject to a terminal disclaimer.

(21) Appl. No.: 17/221,162

(22) Filed: Apr. 2, 2021

(65) Prior Publication Data

US 2021/0220485 A1    Jul. 22, 2021

Related U.S. Application Data

(63) Continuation of application No. 15/780,564, filed as application No. PCT/IB2016/057266 on Dec. 1, 2016, now Pat. No. 10,994,026.

(30) Foreign Application Priority Data

Dec. 3, 2015 (EP) .................................. 15197900

(51) Int. Cl.
| | | |
|---|---|---|
| *C12N 5/00* | (2006.01) | |
| *A61K 48/00* | (2006.01) | |
| *C07K 14/04* | (2006.01) | |
| *C12N 15/86* | (2006.01) | |
| *A61K 41/00* | (2020.01) | |
| *C12N 15/85* | (2006.01) | |
| *C12N 15/864* | (2006.01) | |

(52) U.S. Cl.
CPC ...... *A61K 48/0058* (2013.01); *A61K 41/0057* (2013.01); *A61K 48/0075* (2013.01); *C07K 14/04* (2013.01); *C12N 15/85* (2013.01); *C12N 15/86* (2013.01); *C12N 15/8645* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | |
|---|---|---|
| 9,579,399 B2 | 2/2017 | Roska et al. |
| 9,844,579 B2 | 12/2017 | Balya et al. |
| 9,999,685 B2 | 6/2018 | Roska et al. |
| 10,179,917 B2 | 1/2019 | Roska et al. |
| 10,857,241 B2 | 12/2020 | Roska et al. |
| 10,898,586 B2 | 1/2021 | Hartl et al. |
| 10,941,417 B2 | 3/2021 | Roska et al. |
| 10,994,026 B2 * | 5/2021 | Hartl .................. A61K 41/0057 |
| 10,995,344 B2 | 5/2021 | Hartl et al. |
| 11,059,871 B2 | 7/2021 | Roska et al. |
| 11,371,060 B2 | 1/2022 | Roska et al. |
| 11,254,934 B2 | 2/2022 | Juettner et al. |
| 2003/0097670 A1 | 5/2003 | Palczewski et al. |
| 2009/0088399 A1 | 4/2009 | Balya et al. |
| 2012/0258530 A1 | 10/2012 | Balya et al. |
| 2013/0059374 A1 | 3/2013 | Balya et al. |
| 2018/0125925 A1 | 5/2018 | Balya et al. |
| 2018/0127778 A1 | 5/2018 | Roska et al. |
| 2018/0256753 A1 | 9/2018 | Juettner et al. |
| 2018/0298378 A1 | 10/2018 | Juettner et al. |
| 2018/0346529 A1 | 12/2018 | Hartl et al. |
| 2018/0353617 A1 | 12/2018 | Hartl et al. |
| 2018/0355354 A1 | 12/2018 | Dalkara et al. |
| 2018/0355377 A1 | 12/2018 | Hartl et al. |
| 2019/0054191 A1 | 2/2019 | Hartl et al. |
| 2019/0209708 A1 | 7/2019 | Roska et al. |
| 2019/0276847 A1 | 9/2019 | Hartl et al. |
| 2019/0376082 A1 | 12/2019 | Juettner et al. |
| 2019/0376083 A1 | 12/2019 | Juettner et al. |
| 2020/0277626 A1 | 9/2020 | Roska et al. |
| 2021/0010024 A1 | 1/2021 | Juettner et al. |
| 2021/0054408 A1 | 2/2021 | Juettner et al. |
| 2021/0085804 A1 | 3/2021 | Juettner et al. |

(Continued)

FOREIGN PATENT DOCUMENTS

| | | |
|---|---|---|
| WO | 2008/022772 A1 | 2/2008 |
| WO | 2009/127705 A1 | 10/2009 |

(Continued)

OTHER PUBLICATIONS

Luo (J. Biol. Chem., 1992, vol. 267, No. 34, p. 24738-24747) (Year: 1992).*
Danko (BMC Bioinformatics, Biomed Central, London, GB, vol. 8, No. 1, Oct. 22, 2007, p. 407) (Year: 2007).*
EMBL Database description of JN947423 (Year: 2011).*
U.S. Appl. No. 12/160,277.
U.S. Appl. No. 12/988,336.
U.S. Appl. No. 15/780,557.
U.S. Appl. No. 16/768,055.
U.S. Appl. No. 16/764,306.
U.S. Appl. No. 16/484,252.

(Continued)

*Primary Examiner* — Michael C Wilson
(74) *Attorney, Agent, or Firm* — Joshua. J. Buchman (57) ABSTRACT

The present invention provides an isolated nucleic acid molecule comprising, or consisting of, the nucleic acid sequence of SEQ ID NO:1 or a nucleic acid sequence of at least 300 bp having at least 80% identity to said sequence of SEQ ID NO:1, wherein said isolated nucleic acid molecule specifically leads to the expression in rod photoreceptors of a gene when operatively linked to a nucleic acid sequence coding for said gene.

17 Claims, 1 Drawing Sheet
Specification includes a Sequence Listing.

(56) References Cited

U.S. PATENT DOCUMENTS

| | | | |
|---|---|---|---|
| 2021/0213143 A1 | 7/2021 | Hartl et al. |
| 2021/0220485 A1 | 7/2021 | Hartl et al. |
| 2021/0230634 A1 | 7/2021 | Hartl et al. |
| 2021/0269826 A1 | 9/2021 | Roska et al. |
| 2021/0292792 A1 | 9/2021 | Hartl et al. |
| 2021/0353773 A1 | 11/2021 | Juettner et al. |
| 2021/0355505 A1 | 11/2021 | Juettner et al. |
| 2021/0388385 A1 | 12/2021 | Juettner et al. |
| 2021/0388386 A1 | 12/2021 | Juettner et al. |
| 2021/0388387 A1 | 12/2021 | Juettner et al. |
| 2021/0395750 A1 | 12/2021 | Juettner et al. |
| 2022/0090062 A1 | 3/2022 | Juettner et al. |
| 2022/0119807 A1 | 4/2022 | Juettner et al. |
| 2022/0119841 A1 | 4/2022 | Juettner et al. |
| 2022/0186214 A1 | 6/2022 | Juettner et al. |

FOREIGN PATENT DOCUMENTS

| | | | | |
|---|---|---|---|---|
| WO | 2013/068413 A1 | 5/2013 | | |
| WO | WO-2013068413 A1 * | 5/2013 | ........... | C07K 14/475 |
| WO | 2014/033095 A1 | 3/2014 | | |
| WO | 2015020522 A1 | 2/2015 | | |
| WO | 2015/118507 A1 | 8/2015 | | |
| WO | 2015/121793 A1 | 8/2015 | | |
| WO | 2015143418 A2 | 9/2015 | | |
| WO | 2016/174624 A1 | 11/2016 | | |
| WO | 2017/046084 A1 | 3/2017 | | |
| WO | 2017/064642 A1 | 4/2017 | | |
| WO | 2017/093566 A1 | 6/2017 | | |
| WO | 2017/093931 A1 | 6/2017 | | |
| WO | 2017/093934 A1 | 6/2017 | | |
| WO | 2017/093935 A1 | 6/2017 | | |
| WO | 2017/093936 A1 | 6/2017 | | |
| WO | 2017/199156 A1 | 11/2017 | | |
| WO | 2018/083607 A1 | 5/2018 | | |
| WO | 2018/099974 A1 | 6/2018 | | |
| WO | 2018/099975 A1 | 6/2018 | | |
| WO | 2018/146588 A1 | 8/2018 | | |
| WO | 2019/097454 A1 | 5/2019 | | |
| WO | 2019/106027 A1 | 6/2019 | | |
| WO | 2019/106035 A1 | 6/2019 | | |
| WO | 2020/084537 A1 | 4/2020 | | |
| WO | 2020/084538 A1 | 4/2020 | | |
| WO | 2020/084539 A1 | 4/2020 | | |
| WO | 2020/084540 A1 | 4/2020 | | |
| WO | 2020/084541 A1 | 4/2020 | | |
| WO | 2020/084542 A1 | 4/2020 | | |

OTHER PUBLICATIONS

U.S. Appl. No. 13/300,045.
U.S. Appl. No. 13/614,204.
U.S. Appl. No. 14/421,632.
U.S. Appl. No. 15/005,302.
U.S. Appl. No. 15/117,722.
U.S. Appl. No. 15/117,720.
U.S. Appl. No. 16/768,057.
U.S. Appl. No. 15/811,113.
U.S. Appl. No. 15/760,207.
U.S. Appl. No. 15/767,773.
U.S. Appl. No. 15/570,255.
U.S. Appl. No. 15/780,569.
U.S. Appl. No. 15/781,191.
U.S. Appl. No. 15/780,564.
U.S. Appl. No. 15/780,567.
U.S. Appl. No. 16/302,222.
U.S. Appl. No. 16/346,680.
U.S. Appl. No. 16/464,478.
U.S. Appl. No. 16/464,475.
U.S. Appl. No. 17/084,963.
U.S. Appl. No. 17/155,743.
U.S. Appl. No. 17/172,332.
Hershko et al., "The mouse Snrpn minimal promoter and its human orthologue: activity and imprinting," Genes Cells. 6(11):967-75 (2001).
Luo et al., "Characterization of a minimal promoter element required for transcription of the mouse type II beta regulatory subunit (RII beta) of cAMP-dependent protein kinase," J Biol Chem. 267(34):24738-47 (1992).
Toyoda et al. EM_GSS:GA040648, XP-002757223, (2011) "Mus musculus domesticus DNA, BAC clone: B6Ng01-226N02, 5' end" (Retrieved from the Internet: URL:http://ibis.internal.epo.org/exam/dbfetch.jsp?id=EM_GSS:GA040648 on Feb. 5, 2016), (1 page).
Skarnes et al. EM_STD:JN947423, XP-002757222, (2011) "Mus musculus targeted KO-first, conditional ready, lacZ-tagged mutant allele Shh:tm1a (EUCOMM) Wtsi; transgenic" (Retrieved from the Internet: URL:http://ibis.internal.epo.org/exam/dbfetch.jsp?id=EM_STD:JN947423 on Feb. 5, 2016), (7 pages).
Danko et al. "Bioinformatic identification of novel putative photoreceptor specific cis-elements" BMC Bioinformatics, BioMed Central, (2007), 8:407, pp. 1-16.
Reks et al. "Cooperative activation of Xenopus rhodopsin transcription by paired-like transcription factors" BMC Molecular Biology, (2014), 15:4, pp. 1-14.
Beltran, et al. "rAAV2/5 gene-targeting to rods: dose-dependent efficiency and complications associated with different promoters" Gene Therapy, (2010), vol. 17, pp. 1162-1174.
International Search Report and Written Opinion from PCT/IB2016/057266 dated Feb. 3, 2017 (12 pages).
JN947423: "Mus musculus targeted KO-first, conditional ready, lacZ-tagged mutant allele Shh:tm1a(EUCOMM)Wtsi; transgenic," published Nov. 6, 2011 available at <https://www.ebi.ac.uk/ena/browser/api/embl/JN947423.1> 12 pages.
GA040648: "Mus musculus domesticus DNA, BAC clone: B6Ng01-226N02, 5' end," published Feb. 6, 2011 available at <https://www.ebi.ac.uk/ena/browser/api/embl/ga040648.1> 2 pages.
U.S. Appl. No. 17/223,875.
U.S. Appl. No. 17/287,375.
U.S. Appl. No. 17/287,379.
U.S. Appl. No. 17/287,429.
U.S. Appl. No. 17/287,431.
U.S. Appl. No. 17/287,434.
U.S. Appl. No. 17/287,437.
U.S. Appl. No. 17/342,013.

* cited by examiner

EXPRESSION CASSETTE WITH A SYNP160 PROMOTER

CROSS-REFERENCE TO RELATED APPLICATIONS

This application is a continuation of U.S. patent application Ser. No. 15/780,564, filed on May 31, 2018, which is a U.S. National Phase Application under 35 U.S.C. § 371 of International Patent Application No. PCT/IB2016/057266, filed on Dec. 1, 2016, which claims priority to and the benefit of European Patent Application No. 15197900.2, filed on Dec. 3, 2015, the contents of each of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Apr. 1, 2021 is named PAT057173-US-CNT_SL and is 1,137 bytes in size.

FIELD OF THE INVENTION

The present invention relates to a nucleic acid sequence leading to the expression of genes specifically in rod photoreceptor cells.

BACKGROUND OF THE INVENTION

For expression purposes recombinant genes are usually transfected into the target cells, cell populations or tissues, as cDNA constructs in the context of an active expression cassette to allow transcription of the heterologous gene. The DNA construct is recognized by the cellular transcription machinery in a process that involves the activity of many trans-acting transcription factors (TF) at cis-regulatory elements, including enhancers, silencers, insulators and promoters (herein globally referred to as "promoters").

Gene promoter are involved in all of these levels of regulation, serving as the determinant in gene transcription by integrating the influences of the DNA sequence, transcription factor binding and epigenetic features. They determines the strength of e.g. transgene expression which is encoded by a plasmid vector as well as in which cell type or types said transgene will be expressed. The most common promoters used for driving heterologous gene expression in mammalian cells are the human and mouse cytomegalovirus (CMV) major immediate early promoter. They confer a strong expression and have proved robust in several cell types. Other viral promoters such as the SV40 immediate early promoter and the Rous Sarcoma Virus (RSV) long-terminal-repeat (LTR) promoter are also used frequently in expression cassettes.

Instead of viral promoters, cellular promoters can also be used. Among known promoters are those from house-keeping genes that encode abundantly transcribed cellular transcripts, such as beta-actin, elongation factor 1-alpha (EF-1alpha), or ubiquitin. Compared to viral promoters, eukaryotic gene expression is more complex and requires a precise coordination of many different factors.

One of the aspects concerning the use of endogenous regulatory elements for transgene expression is the generation of stable mRNA and that expression can take place in the native environment of the host cell where trans-acting transcription factors are provided accordingly. Since expression of eukaryotic genes is controlled by a complex machinery of cis- and trans-acting regulatory elements, most cellular promoters suffer from a lack of extensive functional characterization. Parts of the eukaryotic promoter are usually located immediately upstream of its transcribed sequence and serves as the point of transcriptional initiation. The core promoter immediately surrounds the transcription start site (TSS) which is sufficient to be recognized by the transcription machinery. The proximal promoter comprises the region upstream of the core promoter and contains the TSS and other sequence features required for transcriptional regulation. Transcription factors act sequence-specific by binding to regulatory motifs in the promoter and enhancer sequence thereby activating chromatin and histone modifying enzymes that alter nucleosome structure and its position which finally allows initiation of transcription. The identification of a functional promoter is mainly dependent on the presence of associated upstream or downstream enhancer elements.

Another crucial aspect concerning the use of endogenous regulatory elements for transgene expression is that some promoters can act in a cell specific manner and will lead to the expression of the transgene on in cells of a specific type or, depending on the promoter, in cells of a particular subset.

Therefore, one goal of the present invention is to obtain new sequences suitable for expressing recombinant genes in mammal cells with high expression levels and in a cell type specific manner.

Such sequence address a need in the art for retinal cells specific promoters to develop systems for the study of neurodegenerative disorders, vision restoration, drug discovery, tumor therapies and diagnosis of disorders.

SUMMARY OF THE INVENTION

The present inventors have combined epigenetics, bioinformatics and neuroscience to find promoters which, when in the eye, drive gene expression only in rod photoreceptors.

The nucleic acid sequence of the sequence of the invention is:

```
                                            (SEQ ID NO:1)
GGTTGGTGGTTTGCACCTGCTGTGGTACAGAAGGGGAGAGAAAGGGCTG

GCAGGATGGAGCCAGGTGGGTATGGAGGGTGAGAAATGAGAGAAGGGGT

TGGCTGAGGTGGGAATCAGGACACAAAGGGAAGCCAAAGGTGCTCAGCA

AACACTTGGGTTGTCCAATGTTAGCCAAGCTTCTAGGACCTGACTCAAC

GAGCTTCCTACCCTGTAATGTTCTCATGGACCGTTTCTCCAGAAGGCTT

TGGGCAACCAGAAAACCAGATGGCTGGTACGGCTCTCTTCTTCCTCTGA

GGCAGGGGATTTTGTAGAGGATTCTGCTGACTGAGAAGTGGTTCCTCA

CTTCAGAAA.
```

The present invention hence provides an isolated nucleic acid molecule comprising, or consisting of, the nucleic acid sequence of SEQ ID NO:1 or a nucleic acid sequence of at least 300 bp having at least 70% identity to said nucleic acid sequence of SEQ ID NO:1, wherein said isolated nucleic acid molecule specifically leads to the expression in rod photoreceptors of a gene operatively linked to said nucleic acid sequence coding for said gene. In some embodiments, the nucleic acid sequence is at least 300 bp, has at least 80% identity to said nucleic acid sequence of SEQ ID NO:1. In some embodiments, the nucleic acid sequence is at least 300 bp, and has at least 85% identity to said nucleic acid sequence of SEQ ID NO:1. In some embodiments, the nucleic acid sequence is at least 300 bp, and has at least 90% identity to said nucleic acid sequence of SEQ ID NO:1. In some embodiments, the nucleic acid sequence is at least 300 bp, and has at least 95% identity to said nucleic acid sequence of SEQ ID NO:1. In some embodiments, the nucleic acid sequence is at least 300 bp, and has at least 96% identity to said nucleic acid sequence of SEQ ID NO:1. In some embodiments, the nucleic acid sequence is at least 300 bp, and has at least 97% identity to said nucleic acid sequence of SEQ ID NO:1. In some embodiments, the nucleic acid sequence is at least 300 bp, and has at least 98% identity to said nucleic acid sequence of SEQ ID NO:1. In some embodiments, the nucleic acid sequence is at least 300 bp, and has at least 99% identity to said nucleic acid sequence of SEQ ID NO:1. In some embodiments, the nucleic acid sequence is at least 300 bp, and has 100% identity to said nucleic acid sequence of SEQ ID NO:1.

The isolated nucleic acid molecule of the invention can additionally comprise a minimal promoter, for instance a SV40 minimal promoter, e.g. the SV40 minimal promoter or the one used in the examples.

Also provided is an isolated nucleic acid molecule comprising a sequence that hybridizes under stringent conditions to an isolated nucleic acid molecule of the invention as described above.

The present invention also provides an expression cassette comprising an isolated nucleic acid of the invention as described above, wherein said promoter is operatively linked to at least a nucleic acid sequence encoding for a gene to be expressed specifically in rod photoreceptors.

The present invention further provides a vector comprising the expression cassette of the invention. In some embodiments, said vector is a viral vector.

The present invention also encompasses the use of a nucleic acid of the invention, of an expression cassette of the invention or of a vector of the invention for the expression of a gene in rod photoreceptors.

The present invention further provides a method of expressing gene in rod photoreceptors comprising the steps of transfecting an isolated cell, a cell line or a cell population (e.g. a tissue) with an expression cassette of the invention, wherein the gene to be expressed will be expressed by the isolated cell, the cell line or the cell population if said cell is, or said cells comprise, rod photoreceptors. In some embodiments, the isolated cell, cell line or cell population or tissue is human.

The present invention also provides an isolated cell comprising the expression cassette of the invention. In some embodiments, the expression cassette or vector is stably integrated into the genome of said cell.

A typical gene which can be operatively linked to the promoter of the invention is a gene encoding for a halorhodopsin or a channelrhodosin.

In addition, the present invention also provides a kit for expressing gene in rod photoreceptors, which kit comprises an isolated nucleic acid molecule of the invention.

BRIEF DESCRIPTION OF THE DRAWINGS

FIG. 1: Laser-scanning confocal microscope images of EGFP expression from the promoter with SEQ ID NO:1, 3 weeks after subretinal injection of AAV-synP160-ChR2-EGFP in adult C57BL/6 mouse eyes as side projection and top view in photoreceptor layer. Induced expression in rod photoreceptor cells can be observed. Green=EGFP driven by the SEQ ID NO:1, Red=mCAR, White=Hoechst.

DETAILED DESCRIPTION OF THE INVENTION

Figure 1:
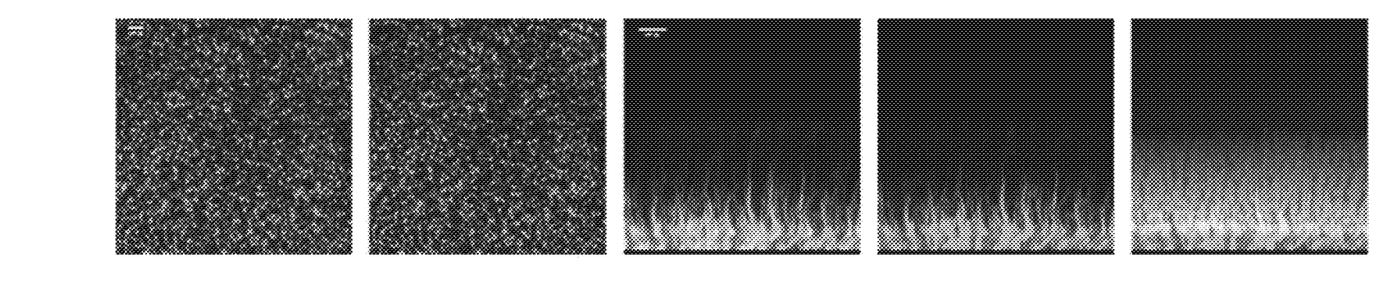

The present inventors have combined epigenetics, bioinformatics and neuroscience to find promoters which, when in the eye, drive gene expression only in rod photoreceptors.

The nucleic acid sequence of the sequence of the invention is:

(SEQ ID NO:1)
GGTTGGTGGTTTGCACCTGCTGTGGTACAGAAGGGGAGAGAAAGGGCTG

GCAGGATGGAGCCAGGTGGGTATGGAGGGTGAGAAATGAGAGAAGGGGT

TGGCTGAGGTGGGAATCAGGACACAAAGGGAAGCCAAAGGTGCTCAGCA

AACACTTGGGTTGTCCAATGTTAGCCAAGCTTCTAGGACCTGACTCAAC

GAGCTTCCTACCCTGTAATGTTCTCATGGACCGTTTCTCCAGAAGGCTT

TGGGCAACCAGAAAACCAGATGGCTGGTACGGCTCTCTTCTTCCTCTGA

GGCAGGGGGATTTTGTAGAGGATTCTGCTGACTGAGAAGTGGTTCCTCA

CTTCAGAAA.

The present invention hence provides an isolated nucleic acid molecule comprising, or consisting of, the nucleic acid sequence of SEQ ID NO:1 or a nucleic acid sequence of at least 300 bp having at least 70% identity to said nucleic acid sequence of SEQ ID NO:1, wherein said isolated nucleic acid molecule specifically leads to the expression in rod photoreceptors of a gene operatively linked to said nucleic acid sequence coding for said gene. In some embodiments, the nucleic acid sequence is at least 300 bp, has at least 80% identity to said nucleic acid sequence of SEQ ID NO:1. In some embodiments, the nucleic acid sequence is at least 300 bp, and has at least 85% identity to said nucleic acid sequence of SEQ ID NO:1. In some embodiments, the nucleic acid sequence is at least 300 bp, and has at least 90% identity to said nucleic acid sequence of SEQ ID NO:1. In some embodiments, the nucleic acid sequence is at least 300 bp, and has at least 95% identity to said nucleic acid sequence of SEQ ID NO:1. In some embodiments, the nucleic acid sequence is at least 300 bp, and has at least 96% identity to said nucleic acid sequence of SEQ ID NO:1. In some embodiments, the nucleic acid sequence is at least 300 bp, and has at least 97% identity to said nucleic acid sequence of SEQ ID NO:1. In some embodiments, the nucleic acid sequence is at least 300 bp, and has at least 98% identity to said nucleic acid sequence of SEQ ID NO:1. In some embodiments, the nucleic acid sequence is at least 300 bp, and has at least 99% identity to said nucleic acid sequence of SEQ ID NO:1. In some embodiments, the nucleic acid sequence is at least 300 bp, and has 100% identity to said nucleic acid sequence of SEQ ID NO:1.

The isolated nucleic acid molecule of the invention can additionally comprise a minimal promoter, for instance a SV40 minimal promoter, e.g. the SV40 minimal promoter or the one used in the examples.

Also provided is an isolated nucleic acid molecule comprising a sequence that hybridizes under stringent conditions to an isolated nucleic acid molecule of the invention as described above. The present invention also provides an expression cassette comprising an isolated nucleic acid of the invention as described above, wherein said promoter is operatively linked to at least a nucleic acid sequence encoding for a gene to be expressed specifically in rod photoreceptors.

The present invention further provides a vector comprising the expression cassette of the invention. In some embodiments, said vector is a viral vector.

The present invention also encompasses the use of a nucleic acid of the invention, of an expression cassette of the invention or of a vector of the invention for the expression of a gene in rod photoreceptors.

The present invention further provides a method of expressing gene in rod photoreceptors comprising the steps of transfecting an isolated cell, a cell line or a cell population (e.g. a tissue) with an expression cassette of the invention, wherein the gene to be expressed will be expressed by the isolated cell, the cell line or the cell population if said cell is, or said cells comprise, rod photoreceptors. In some embodiments, the isolated cell, cell line or cell population or tissue is human.

The present invention also provides an isolated cell comprising the expression cassette of the invention. In some embodiments, the expression cassette or vector is stably integrated into the genome of said cell.

A typical gene which can be operatively linked to the promoter of the invention is a gene encoding for a halorhodopsin or a channelrhodosin.

In addition, the present invention also provides a kit for expressing gene in rod photoreceptors, which kit comprises an isolated nucleic acid molecule of the invention.

As used herein, the term "promoter" refers to any cis-regulatory elements, including enhancers, silencers, insulators and promoters. A promoter is a region of DNA that is generally located upstream (towards the 5' region) of the gene that is needed to be transcribed. The promoter permits the proper activation or repression of the gene which it controls. In the context of the present invention, the promoters lead to the specific expression of genes operably linked to them in the rod photoreceptors. "Specific expression", also referred to as "expression only in a certain type of cell" means that at least more than 75% of the cells expressing the gene of interest are of the type specified, i.e. rod photoreceptors in the present case.

Expression cassettes are typically introduced into a vector that facilitates entry of the expression cassette into a host cell and maintenance of the expression cassette in the host cell. Such vectors are commonly used and are well known to those of skill in the art. Numerous such vectors are commercially available, e. g., from Invitrogen, Stratagene, Clontech, etc., and are described in numerous guides, such as Ausubel, Guthrie, Strathem, or Berger, all supra. Such vectors typically include promoters, polyadenylation signals, etc. in conjunction with multiple cloning sites, as well as additional elements such as origins of replication, selectable marker genes (e. g., LEU2, URA3, TRP 1, HIS3, GFP), centromeric sequences, etc.

Viral vectors, for instance an AAV, a PRV or a lentivirus, are suitable to target and deliver genes to rod photoreceptors using a promoter of the invention.

The output of retinal cells can be measured using an electrical method, such as a multi-electrode array or a patch-clamp, or using a visual method, such as the detection of fluorescence.

The methods using nucleic acid sequence of the invention can be used for identifying therapeutic agents for the treatment of a neurological disorder or of a disorder of the retina involving rod photoreceptors, said method comprising the steps of contacting a test compound with rod photoreceptors expressing one or more transgene under a promoter of the invention, and comparing at least one output of rod photoreceptors obtained in the presence of said test compound with the same output obtained in the absence of said test compound.

Moreover, the methods using promoters of the invention can also be used for in vitro testing of vision restoration, said method comprising the steps of contacting rod photoreceptors expressing one or more transgene under the control of a promoter of the invention with an agent, and comparing at least one output obtained after the contact with said agent with the same output obtained before said contact with said agent.

Channelrhodopsins are a subfamily of opsin proteins that function as light-gated ion channels. They serve as sensory photoreceptors in unicellular green algae, controlling phototaxis, i.e. movement in response to light. Expressed in cells of other organisms, they enable the use of light to control intracellular acidity, calcium influx, electrical excitability, and other cellular processes. At least three "natural" channelrhodopsins are currently known: Channelrhodopsin-1 (ChR1), Channelrhodopsin-2 (ChR2), and Volvox Channelrhodopsin (VChR1). Moreover, some modified/improved versions of these proteins also exist. All known Channelrhodopsins are unspecific cation channels, conducting H+, Na+, K+, and Ca2+ ions.

Halorhodopsin is a light-driven ion pump, specific for chloride ions, and found in phylogenetically ancient "bacteria" (archaea), known as halobacteria. It is a seven-transmembrane protein of the retinylidene protein family, homologous to the light-driven proton pump bacteriorhodopsin, and similar in tertiary structure (but not primary sequence structure) to vertebrate rhodopsins, the pigments that sense light in the retina. Halorhodopsin also shares sequence similarity to channelrhodopsin, a light-driven ion channel. Halorhodopsin contains the essential light-isomerizable vitamin A derivative all-trans-retinal. Halorhodopsin is one of the few membrane proteins whose crystal structure is known. Halorhodopsin isoforms can be found in multiple species of halobacteria, including *H. salinarum*, and *N. pharaonis*. Much ongoing research is exploring these differences, and using them to parse apart the photocycle and pump properties. After bacteriorhodopsin, halorhodopsin may be the best type I (microbial) opsin studied. Peak absorbance of the halorhodopsin retinal complex is about 570 nm. Recently, halorhodopsin has become a tool in optogenetics. Just as the blue-light activated ion channel channelrhodopsin-2 opens up the ability to activate excitable cells (such as neurons, muscle cells, pancreatic cells, and immune cells) with brief pulses of blue light, halorhodopsin opens up the ability to silence excitable cells with brief pulses of yellow light. Thus halorhodopsin and channelrhodopsin together enable multiple-color optical activation, silencing, and desynchronization of neural activity, creating a powerful neuroengineering toolbox.

In some embodiments, the promoter is part of a vector targeted a retina, said vector expressing at least one reporter gene which is detectable in living rod photoreceptors.

Suitable viral vectors for the invention are well-known in the art. For instance an AAV, a PRV or a lentivirus, are suitable to target and deliver genes to rod photoreceptors.

When working with isolated retina, optimal viral delivery for retinal cells can be achieved by mounting the ganglion cell side downwards, so that the photoreceptor side of the retina is exposed and can thus be better transfected. Another technique is slicing, e.g. with a razor blade, the inner limiting membrane of the retina, such that the delivering viruses can penetrate the inner membranes. A further way is to embed the retina in agar, slicing said retina and applying the delivery viruses from the side of the slice.

The output of transfected cells can be measured using well-known methods, for instance using an electrical method, such as a multi-electrode array or a patch-clamp, or using a visual method, such as the detection of fluorescence. In some cases, the inner limiting membrane is removed by micro-surgery the inner limiting membrane. In other cases, recording is achieved through slices performed to the inner limiting membrane.

Any source of retinal cells can be used for the present invention. In some embodiments of the invention, the retinal cells come from, or are in, a human retina. In other embodiments, the retina is from an animal, e.g. of bovine or of rodent origin. Human retina can be easily obtained from cornea banks where said retinas are normally discarded after the dissection of the cornea. Adult human retina has a large surface (about 1100 mm$^2$) and can therefore be easily separated to a number of experimentally subregions. Moreover, retinas can also be used as an exquisite model for synaptic communication since the retina has synapses that are identical to the rest of the brain.

As used herein, the term "animal" is used herein to include all animals. In some embodiments of the invention, the non-human animal is a vertebrate. Examples of animals are human, mice, rats, cows, pigs, horses, chickens, ducks, geese, cats, dogs, etc. The term "animal" also includes an individual animal in all stages of development, including embryonic and fetal stages. A "genetically-modified animal" is any animal containing one or more cells bearing genetic information altered or received, directly or indirectly, by deliberate genetic manipulation at a sub-cellular level, such as by targeted recombination, microinjection or infection with recombinant virus. The term "genetically-modified animal" is not intended to encompass classical crossbreeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germline genetically-modified animal" refers to a genetically-modified animal in which the genetic alteration or genetic information was introduced into germline cells, thereby conferring the ability to transfer the genetic information to its offspring. If such offspring in fact possess some or all of that alteration or genetic information, they are genetically-modified animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The genes used for altering a target gene may be obtained by a wide variety of techniques that include, but are not limited to, isolation from genomic sources, preparation of cDNAs from isolated mRNA templates, direct synthesis, or a combination thereof.

A type of target cells for transgene introduction is the ES cells. ES cells may be obtained from pre-implantation embryos cultured in vitro and fused with embryos (Evans et al. (1981), Nature 292:154-156; Bradley et al. (1984), Nature 309:255-258; Gossler et al. (1986), Proc. Natl. Acad. Sci. USA 83:9065-9069; Robertson et al. (1986), Nature 322:445-448; Wood et al. (1993), Proc. Natl. Acad. Sci. USA 90:4582-4584). Transgenes can be efficiently introduced into the ES cells by standard techniques such as DNA transfection using electroporation or by retrovirus-mediated transduction. The resultant transformed ES cells can thereafter be combined with morulas by aggregation or injected into blastocysts from a non-human animal. The introduced ES cells thereafter colonize the embryo and contribute to the germline of the resulting chimeric animal (Jaenisch (1988), Science 240:1468-1474). The use of gene-targeted ES cells in the generation of gene-targeted genetically-modified mice was described 1987 (Thomas et al. (1987), Cell 51:503-512) and is reviewed elsewhere (Frohman et al. (1989), Cell 56:145-147; Capecchi (1989), Trends in Genet. 5:70-76; Baribault et al. (1989), Mol. Biol. Med. 6:481-492; Wagner (1990), EMBO J. 9:3025-3032; Bradley et al. (1992), Bio/Technology 10:534-539).

Techniques are available to inactivate or alter any genetic region to any mutation desired by using targeted homologous recombination to insert specific changes into chromosomal alleles. As used herein, a "targeted gene" is a DNA sequence introduced into the germline of a non-human animal by way of human intervention, including but not limited to, the methods described herein. The targeted genes of the invention include DNA sequences which are designed to specifically alter cognate endogenous alleles.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome removed from a cell or a cell lysate (e.g., a "chromosome spread", as in a karyotype), or a preparation of randomly sheared genomic DNA or a preparation of genomic DNA cut with one or more restriction enzymes is not "isolated" for the purposes of this invention. As discussed further herein, isolated nucleic acid molecules according to the present invention may be produced naturally, recombinantly, or synthetically.

"Polynucleotides" can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotides can be composed of triplestranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The expression "polynucleotide encoding a polypeptide" encompasses a polynucleotide which includes only coding sequence for the polypeptide as well as a polynucleotide which includes additional coding and/or non-coding sequence.

"Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 50 degree C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37 degree C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The terms "fragment," "derivative" and "analog" when referring to polypeptides means polypeptides which either retain substantially the same biological function or activity as such polypeptides. An analog includes a pro-protein which can be activated by cleavage of the pro-protein portion to produce an active mature polypeptide.

The term "gene" means the segment of DNA involved in producing a polypeptide chain; it includes regions preceding and following the coding region "leader and trailer" as well as intervening sequences (introns) between individual coding segments (exons).

Polypeptides can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include, but are not limited to, acetylation, acylation, biotinylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, denivatization by known protecting/blocking groups, disulfide bond formation, demethylation, formation of covalent cross-links, formation of cysteine, formation of pyroglutamate, formylation, gamma-carboxylation, glycosylation, GPI anchor formation, hydroxylation, iodination, linkage to an antibody molecule or other cellular ligand, methylation, myristoylation, oxidation, pegylation, proteolytic processing (e.g., cleavage), phosphorylation, prenylation, racemization, selenoylation, sulfation, transfer-RNA mediated addition of amino acids to proteins such as arginylation, and ubiquitination. (See, for instance, PROTEINS-STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth Enzymol 182: 626-646 (1990); Rattan et al., Ann NY Acad Sci 663:48-62 (1992).)

A polypeptide fragment "having biological activity" refers to polypeptides exhibiting activity similar, but not necessarily identical to, an activity of the original polypeptide, including mature forms, as measured in a particular biological assay, with or without dose dependency. In the case where dose dependency does exist, it need not be identical to that of the polypeptide, but rather substantially similar to the dose-dependence in a given activity as compared to the original polypeptide (i.e., the candidate polypeptide will exhibit greater activity or not more than about 25-fold less and, in some embodiments—not more than about tenfold less activity, or not more than about three-fold less activity relative to the original polypeptide.)

Species homologs may be isolated and identified by making suitable probes or primers from the sequences provided herein and screening a suitable nucleic acid source for the desired homologue.

"Variant" refers to a polynucleotide or polypeptide differing from the original polynucleotide or polypeptide, but retaining essential properties thereof. Generally, variants are overall closely similar, and, in many regions, identical to the original polynucleotide or polypeptide.

As a practical matter, whether any particular nucleic acid molecule or polypeptide is at least 80%, 85%, 90%, 92%, 95%, 96%, 97%, 98%, 99%, or 100% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Blosci. (1990) 6:237-245). In a sequence alignment the query and subject sequences are both DNA sequences. An RNA sequence can be compared by converting U's to Ts. The result of said global sequence alignment is in percent identity. Preferred parameters used in a FASTDB alignment of DNA sequences to calculate percent identity are: Matrix=Unitary, k-tuple=4, Mismatch Penalty—1, Joining Penalty—30, Randomization Group Length=0, Cutoff Score=I, Gap Penalty—5, Gap Size Penalty 0.05, Window Size=500 or the length of the subject nucleotide sequence, whichever is shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 impaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98%, 99%, or 100% identical to, for instance, the amino acid sequences shown in a sequence or to the amino acid sequence encoded by deposited DNA clone can be determined conventionally using known computer programs. A preferred method for determining, the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty—I, Joining Penalty=20, Randomization Group Length=0, Cutoff Score=I, Window Size=sequence length, Gap Penalty—5, Gap Size Penalty—0.05, Window Size=500 or the length of the subject amino acid sequence, whichever is shorter. If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. Only residue positions outside the N- and C-terminal ends of the subject sequence, as displayed in the FASTDB alignment, which are not matched/aligned with the query sequence are manually corrected for. No other manual corrections are to be made for the purposes of the present invention.

Naturally occurring protein variants are called "allelic variants," and refer to one of several alternate forms of a gene occupying a given locus on a chromosome of an organism. (Genes 11, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like.

A "fluorescent label" refers to any label with the ability to emit light of a certain wavelength when activated by light of another wavelength.

"Fluorescence" refers to any detectable characteristic of a fluorescent signal, including intensity, spectrum, wavelength, intracellular distribution, etc.

"Detecting" fluorescence refers to assessing the fluorescence of a cell using qualitative or quantitative methods. In some of the embodiments of the present invention, fluorescence will be detected in a qualitative manner. In other words, either the fluorescent marker is present, indicating that the recombinant fusion protein is expressed, or not. For other instances, the fluorescence can be determined using quantitative means, e. g., measuring the fluorescence intensity, spectrum, or intracellular distribution, allowing the statistical comparison of values obtained under different conditions. The level can also be determined using qualitative methods, such as the visual analysis and comparison by a human of multiple samples, e. g., samples detected using a fluorescent microscope or other optical detector (e. g., image analysis system, etc.). An "alteration" or "modulation" in fluorescence refers to any detectable difference in the intensity, intracellular distribution, spectrum, wavelength, or other aspect of fluorescence under a particular condition as compared to another condition. For example, an "alteration" or "modulation" is detected quantitatively, and the difference is a statistically significant difference. Any "alterations" or "modulations" in fluorescence can be detected using standard instrumentation, such as a fluorescent microscope, CCD, or any other fluorescent detector, and can be detected using an automated system, such as the integrated systems, or can reflect a subjective detection of an alteration by a human observer.

The "green fluorescent protein" (GFP) is a protein, composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostablility and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted ε), also known as its optical cross section of $9.13 \times 10\text{-}21$ m$^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

As used herein, the singular forms "a", "an," and "the" include plural reference unless the context clearly dictates otherwise.

A "virus" is a sub-microscopic infectious agent that is unable to grow or reproduce outside a host cell. Each viral particle, or virion, consists of genetic material, DNA or RNA, within a protective protein coat called a capsid. The capsid shape varies from simple helical and icosahedral (polyhedral or near-spherical) forms, to more complex structures with tails or an envelope. Viruses infect cellular life forms and are grouped into animal, plant and bacterial types, according to the type of host infected.

The term "transsynaptic virus" as used herein refers to viruses able to migrate from one neurone to another connecting neurone through a synapse. Examples of such transsynaptic virus are rhabodiviruses, e.g. rabies virus, and alphaherpesviruses, e.g. pseudorabies or herpes simplex virus. The term "transsynaptic virus" as used herein also encompasses viral sub-units having by themselves the capacity to migrate from one neurone to another connecting neurone through a synapse and biological vectors, such as modified viruses, incorporating such a sub-unit and demonstrating a capability of migrating from one neurone to another connecting neurone through a synapse.

Transsynaptic migration can be either anterograde or retrograde. During a retrograde migration, a virus will travel from a postsynaptic neuron to a presynaptic one. Accordingly, during anterograde migration, a virus will travel from a presynaptic neuron to a postsynaptic one.

Homologs refer to proteins that share a common ancestor. Analogs do not share a common ancestor, but have some functional (rather than structural) similarity that causes them to be included in a class (e.g. trypsin like serine proteinases and subtilisin's are clearly not related—their structures outside the active site are completely different, but they have virtually geometrically identical active sites and thus are considered an example of convergent evolution to analogs).

There are two subclasses of homologs—orthologs and paralogs. Orthologs are the same gene (e.g. cytochome 'c'), in different species. Two genes in the same organism cannot be orthologs. Paralogs are the results of gene duplication (e.g. hemoglobin beta and delta). If two genes/proteins are homologous and in the same organism, they are paralogs.

As used herein, the term "disorder" refers to an ailment, disease, illness, clinical condition, or pathological condition.

As used herein, the term "pharmaceutically acceptable carrier" refers to a carrier medium that does not interfere with the effectiveness of the biological activity of the active ingredient, is chemically inert, and is not toxic to the patient to whom it is administered.

As used herein, the term "pharmaceutically acceptable derivative" refers to any homolog, analog, or fragment of an agent, e.g. identified using a method of screening of the invention, that is relatively non-toxic to the subject.

The term "therapeutic agent" refers to any molecule, compound, or treatment, that assists in the prevention or treatment of disorders, or complications of disorders.

Compositions comprising such an agent formulated in a compatible pharmaceutical carrier may be prepared, packaged, and labeled for treatment.

If the complex is water-soluble, then it may be formulated in an appropriate buffer, for example, phosphate buffered saline or other physiologically compatible solutions.

Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e. g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

The compounds may be formulated for parenteral administration by injection, e.g., by bolus injection or continuous infusion. Formulations for injection may be presented in unit dosage form, e.g., in ampoules or in multi-dose containers, with an added preservative.

The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated as a topical application, such as a cream or lotion.

In addition to the formulations described previously, the compounds may also be formulated as a depot preparation. Such long acting formulations may be administered by implantation (for example, intraocular, subcutaneous or intramuscular) or by intraocular injection.

Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the compositions in pharmaceutically acceptable form.

The composition in a vial of a kit may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit further comprises a needle or syringe, preferably packaged in sterile form, for injecting the complex, and/or a packaged alcohol pad. Instructions are optionally included for administration of compositions by a clinician or by the patient.

Rod photoreceptors, rod cells, or rods, are photoreceptor cells in the retina of the eye that can function in less intense light than the other type of visual photoreceptor, cone cells. Rods are concentrated at the outer edges of the retina and are used in peripheral vision. On average, there are approximately 90 million rod cells in the human retina. More sensitive than cone cells, rod cells are almost entirely responsible for night vision. However, because they have only one type of light-sensitive pigment, rather than the three types that human cone cells have, rods have little, if any, role in color vision.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Gene Construct

Whole genome high resolution DNA methylation maps were generated in the cell type of interest (rod) to identify candidate regulatory regions. Candidate enhancers were selected based on the presence of cell type specific DNA hypomethylation. The so-selected elements were screened for expression using an in vivo high throughput reporter assay in cones and rods. Rod specific sequence elements were then synthetized and cloned in front of a minimal promotor sequence

```
                                              (SEQ ID NO:2)
ATCCTCACATGGTCCTGCTGGAGTTAGTAGAGGGTATATAATGGAAGCT

CGACTTCCAGCTATCACATCCACTGTGTTGTTGTGAACTGGAATCCACT

ATAGGCCA. ChR2-eGFP
``` coding sequence was inserted immediately after this promoter and the optimized Kozak sequence (GCCACC), and followed by a woodchuck hepatitis virus posttranscriptional regulatory element (WPRE) and SV40 polyadenylation site. Retinal neurons were targeted using AAVs serotype 2/8 with a titer in the range of 3.43E+11 to 1.75E+12 GC/mL.

Viral Transfection and Tissue Preparation

For AAV administration, the eyes of anesthetized animals were punctured in the sclera close to the lens by a sharp 30 gauge needle. 2 microL of AAV particle suspension were injected subretinally by a Hamilton syringe. After 3 weeks, the isolated retinas were fixed for 30 min in 4% PFA in PBS, followed by a washing step in PBS at 4° C. Whole retinas were treated with 10% normal donkey serum (NDS), 1% BSA, 0.5% Triton X-100 in PBS for 1 h at room temperature. Treatment with monoclonal rat anti-GFP antibody (Molecular Probes Inc.; 1:500) and polyclonal rabbit anti-mouse Cone Arrestin antibody (Millipore: 1:200) in 3% NDS, 1% BSA, 0.5% Triton X-100 in PBS was carried out for 5 days at room temperature. Treatment with secondary donkey anti-rat Alexa Fluor-488 Ab (Molecular Probes Inc.; 1:200), anti-rabbit Alexa Fluor-633 and Hoechst, was done for 2 hr. Sections were washed, mounted with ProLong Gold antifade reagent (Molecular Probes Inc.) on glass slides, and photographed using a Zeiss LSM 700 Axio Imager Z2 laser scanning confocal microscope (Carl Zeiss Inc.).

The invention claimed is:

1. An isolated expression cassette comprising: a nucleic acid sequence encoding a protein; and a promoter of at least 300 base pairs and having at least 80% identity to the sequence of SEQ ID NO:1, wherein the promoter is heterologous to the nucleic acid sequence encoding a protein and is capable of driving functional expression of the protein in a cell.

2. The expression cassette of claim 1, wherein the promoter has at least 95% identity to the sequence of SEQ ID NO:1.

3. The expression cassette of claim 1, wherein the promoter comprises the nucleic acid sequence of SEQ ID NO:1.

4. The expression cassette of claim 1, further comprising a minimal promoter.

5. The expression cassette of claim 4, wherein the minimal promoter comprises the nucleic acid sequence of SEQ ID NO:2.

6. A vector comprising the expression cassette of claim 1.

7. The vector of claim 6, wherein said vector is a viral vector.

8. The vector of claim 7, wherein the viral vector is an adeno-associated virus (AAV) vector.

9. An isolated cell comprising the expression cassette of claim 1.

10. The isolated cell of claim 9, wherein the expression cassette is stably integrated into the genome of said cell.

11. The expression cassette of claim 1, wherein the protein is halorhodopsin or channelrhodopsin.

12. The expression cassette of claim 1, wherein the cell is a human cell.

13. The expression cassette of claim 1, wherein the cell is a rodent cell.

14. A method of a expressing a protein in a cell, the method comprising transfecting an isolated cell, a cell line, or a cell population with the expression cassette of claim 1 such that the isolated cell, the cell line, or the cell population expresses the protein.

15. The method of claim 14, wherein the isolated cell is a human cell, or the cell line or the cell population comprises human cells.

16. The method of claim 14, wherein the isolated cell is a rodent cell, or the cell line or the cell population comprises rodent cells.

17. A kit for expressing a protein in a cell, the kit comprising the expression cassette of claim 1.

* * * * *

SEQUENCE LISTING

```
<160> NUMBER OF SEQ ID NOS: 2

<210> SEQ ID NO 1
<211> LENGTH: 352
<212> TYPE: DNA
<213> ORGANISM: Mus musculus

<400> SEQUENCE: 1
ggttggtggt ttgcacctgc tgtggtacag aaggggagag aaagggctgg caggatggag      60
ccaggtgggt atggagggtg agaaatgaga gaaggggttg gctgaggtgg gaatcaggac     120
acaaagggaa gccaaaggtg ctcagcaaac acttgggttg tccaatgtta gccaagcttc     180
taggacctga ctcaacgagc ttcctaccct gtaatgttct catggaccgt ttctccagaa     240
ggctttgggc aaccagaaaa ccagatggct ggtacggctc tcttcttcct ctgaggcagg     300
gggattttgt agaggattct gctgactgag aagtggttcc tcacttcaga aa             352

<210> SEQ ID NO 2
<211> LENGTH: 106
<212> TYPE: DNA
<213> ORGANISM: Mus musculus

<400> SEQUENCE: 2
atcctcacat ggtcctgctg gagttagtag agggtatata atggaagctc gacttccagc      60
tatcacatcc actgtgttgt tgtgaactgg aatccactat aggcca                    106
```